United States Patent [19]

Glassey

[11] Patent Number: 5,423,302
[45] Date of Patent: Jun. 13, 1995

[54] FUEL INJECTION CONTROL SYSTEM HAVING ACTUATING FLUID VISCOSITY FEEDBACK

[75] Inventor: Stephen F. Glassey, East Peoria, Ill.

[73] Assignee: Caterpillar Inc., Peoria, Ill.

[21] Appl. No.: 217,038

[22] Filed: Mar. 23, 1994

[51] Int. Cl.⁶ ............................................. F02M 37/04
[52] U.S. Cl. ................................ 123/446; 123/381; 73/54.31
[58] Field of Search ............... 123/446, 381, 500, 501, 123/357; 73/119 A, 54.31, 54.33, 54.42

[56] References Cited

U.S. PATENT DOCUMENTS

| | | |
|---|---|---|
| 3,170,503 | 2/1965 | Isley et al. . |
| 3,204,623 | 9/1965 | Isley et al. . |
| 3,483,855 | 12/1969 | Thoma . |
| 4,129,034 | 12/1978 | Niles et al. . |
| 4,174,694 | 11/1979 | Wessel ................................. 123/381 |
| 4,252,097 | 2/1981 | Hartford et al. . |
| 4,766,864 | 8/1988 | Ban et al. . |
| 4,889,092 | 12/1989 | Bostwick . |
| 4,955,345 | 9/1990 | Brown et al. . |
| 5,024,200 | 6/1991 | Free et al. . |
| 5,027,768 | 7/1991 | Saegusa ................................ 123/381 |
| 5,060,619 | 10/1991 | Sakurai et al. . |
| 5,085,198 | 2/1992 | Bartlett et al. . |
| 5,121,730 | 6/1992 | Ausman et al. . |
| 5,150,684 | 9/1992 | Jun ....................................... 123/446 |
| 5,176,115 | 1/1993 | Campion . |
| 5,181,494 | 1/1993 | Ausman et al. . |
| 5,191,867 | 3/1993 | Glassey . |
| 5,297,523 | 3/1994 | Hafner ................................. 123/446 |
| 5,357,912 | 10/1994 | Barnes ................................. 123/446 |

*Primary Examiner*—Carl S. Miller
*Attorney, Agent, or Firm*—Joseph W. Keen

[57] ABSTRACT

An apparatus and method for detecting the viscosity of actuating fluid used to actuate a hydraulically-actuated electronically-controlled injector is disclosed. In an internal combustion engine system including an engine having a crankshaft, a crankshaft angular speed sensor responsive to rotation of the crankshaft, a voltage sensor, and an engine coolant temperature sensor, which respectively generate angular speed, voltage, and temperature indicative signals, are provided. An electronic control module is provided with a memory means, the control module having an associated viscosity indicative signal or parameter whose magnitude is representative of the actuating fluid viscosity and is a function of the angular speed, and voltage indicative signals. The actuating fluid viscosity value is used by electronic control module to vary the actuating fluid pressure and vary a fuel delivery command signal pulsewidth and the timing of the application of the fuel delivery command signal relative to a predetermined crankshaft angular position to control the injection of fuel into engine via the injector independent of engine speed and load.

15 Claims, 2 Drawing Sheets

FUEL INJECTION CONTROL SYSTEM HAVING ACTUATING FLUID VISCOSITY FEEDBACK

TECHNICAL FIELD

The present invention relates generally to fuel injection systems and, more particularly to hydraulically-actuated electronically-controlled fuel injection systems.

BACKGROUND ART

The viscosity of the pressurized actuating fluid used to hydraulically actuate an intensifier piston/plunger combination in a hydraulically-actuated unit fuel injector varies with the temperature of the actuating fluid. The magnitude of pressure drops in the actuating fluid circuit vary in accordance with the actuating fluid viscosity, thus affecting the amount of fuel delivered to the engine and the timing of the injection event relative to a predetermined engine crankshaft angle. The viscosity of the actuating fluid is highest under cold engine starting conditions, which results in fuel injection quantity and fuel injection pressure being greatly reduced and the timing of the fuel injection being retarded. Under these extreme conditions, engine starting is difficult.

One approach for solving these problems is to measure the ambient temperature of the fluid, determine a typical viscosity from the measured temperature, and make corrections to delivery, timing and pressure parameters to compensate for the increased viscosity. A problem arises, however, when engine lubrication oil is used as the actuating fluid. In such a system, the user generally controls the type and grade of oil and thus, even for a particular temperature, the viscosity of the engine lubrication oil/actuating fluid varies greatly. Since a temperature measurement alone is inadequate to measure viscosity, fuel injection quantity, timing and pressure parameters are incorrectly determined to compensate for the variation in the viscosity of the actuating fluid, which leads to less than optimal performance of the engine system.

The present invention is directed to overcoming one or more of the problems as set forth above.

DISCLOSURE OF THE INVENTION

This invention provides for smooth and reliable engine starting under all temperature conditions by detecting the viscosity of the actuating fluid via system battery voltage and engine speed. In general, the actuating fluid viscosity is primarily determined by the viscose loads seen by a selected movable engine component as it shears through the actuating fluid. Further, the extreme cold conditions that cause the actuating fluid viscosity to increase will typically result in a reduced battery output voltage, which also results in a reduced engine speed. Accordingly, in one aspect of this invention, the actuating fluid viscosity is determined as a function of the observed engine speed during starting and the battery voltage.

The actuating fluid viscosity affects the fuel injection timing, quantity and pressure characteristics of a hydraulically-actuated injector. Thus, the determined actuating fluid viscosity may be advantageously used to adjust fuel injection parameters in an internal combustion engine system. In another aspect of this invention, the regulated pressure of the actuating fluid supplied to the injector(s), the fuel injection timing and the injector on-time, or pulsewidth are varied as a function of the determined actuating fluid viscosity.

In a hydraulically-actuated fuel injector wherein the actuating fluid is engine lubrication oil, the actuating fluid viscosity varies with the temperature of the actuating fluid and affects the magnitude of pressure drops in the actuating fluid circuit. Variations in actuating fluid viscosity also vary significantly with the type and grade of engine lubricating oil used by the customer. The extent of this variation cannot be determined beforehand and incorporated into the fuel injector system to properly control fuel timing, quantity and pressure parameters. The present invention provides for directly determining, in real time, the actual viscosity of the actuating fluid to thereby provide the means for improving the performance of an engine system in which such hydraulically-actuated electronically-controlled injectors are used. The present invention further provides a method of operating an internal combustion engine system by directly determining the viscosity of the actuating fluid and varying fuel injection parameters to obtain optimal engine system performance.

BEST MODE FOR CARRYING OUT THE INVENTION

Figure 1:
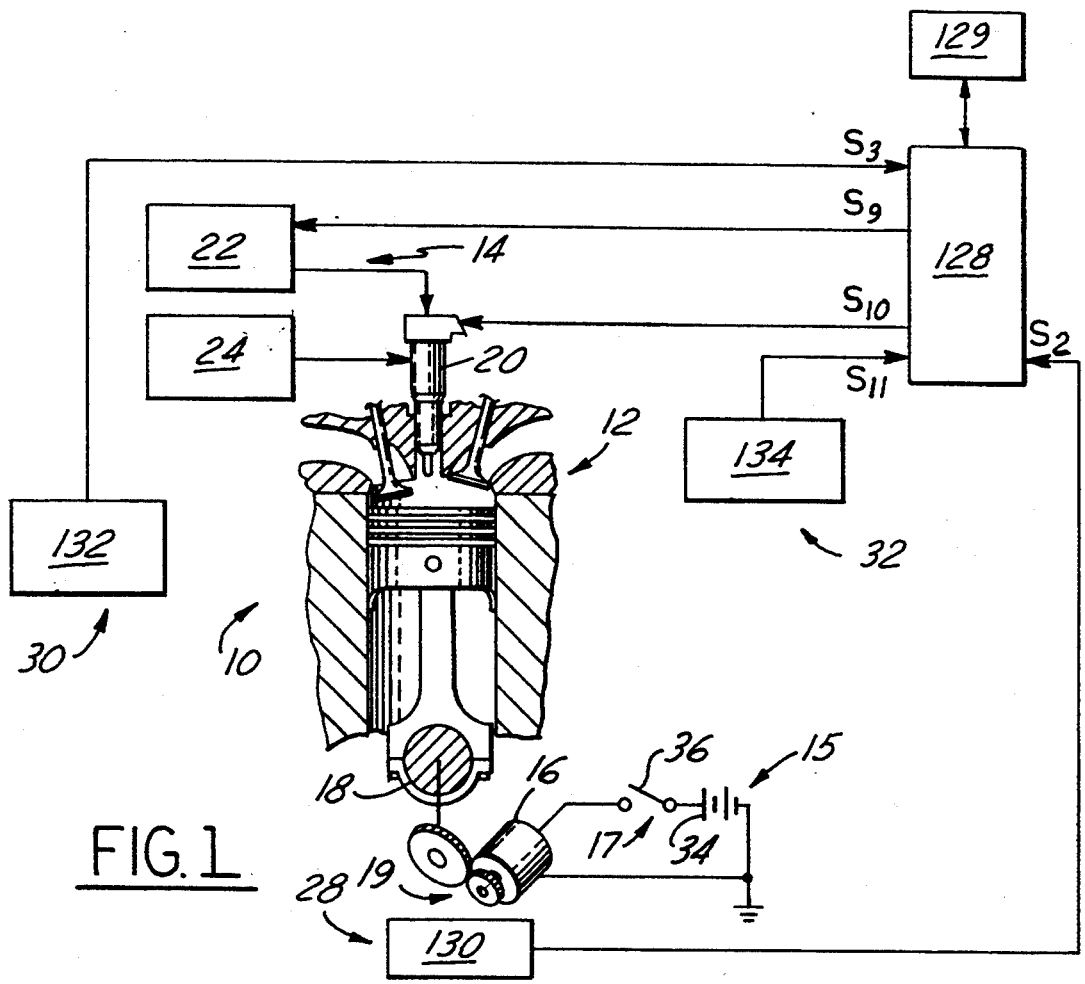
FIG. 1 is a combined block and diagrammatic view of an apparatus according to the present invention for detecting the viscosity of actuating fluid.

Referring now to the drawings wherein like reference numerals refer to identical components in the various views, FIG. 1 shows an internal combustion engine system 10 including an internal combustion engine 12, a hydraulically-actuated electronically-controlled injector fuel system 14, means 15 for providing starter motor voltage, an engine starter motor 16, and means 17 for selectively applying engine starter voltage.

The exemplary engine 12, only partially shown in FIG. 1, may be, for example, a diesel-cycle direct-injection internal combustion engine. The engine 12 includes a rotatable crankshaft 18. Coupling means 19 connects starter motor 16 to crankshaft 18 and preferably takes the form of a conventional drive gear train assembly.

Figure 2:
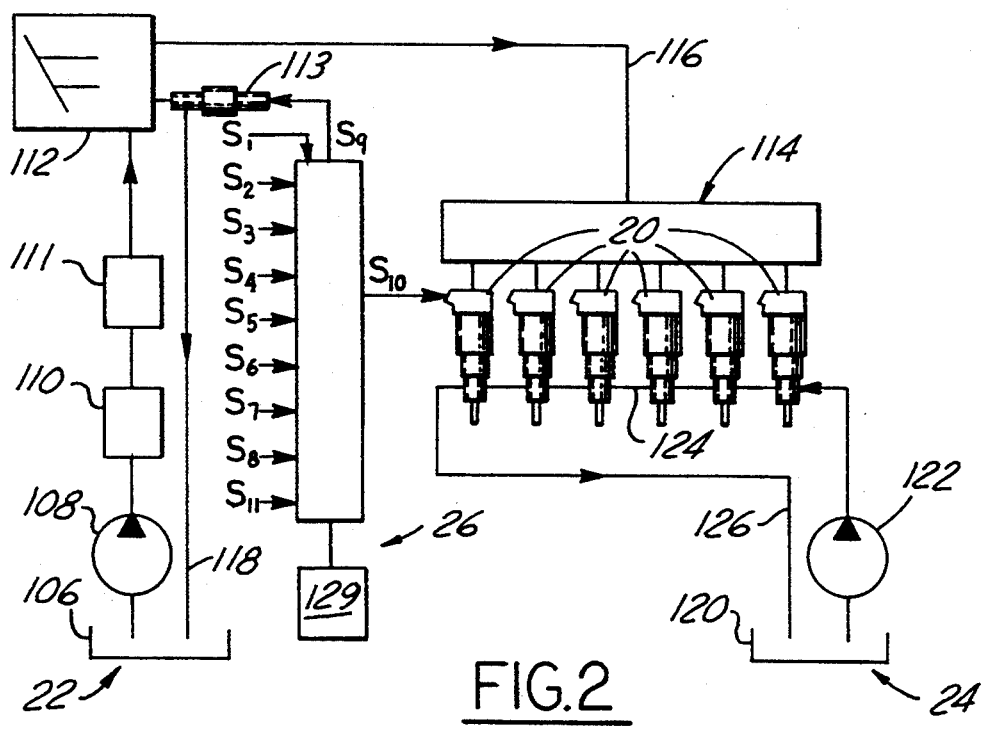
FIG. 2 is a combined block and schematic view of a hydraulically-actuated electronically-controlled injector fuel system, including an actuating fluid circuit and a fuel supply circuit.

As shown in FIG. 2, fuel system 14 includes at least one hydraulically-actuated electronically-controlled injector 20 for each combustion chamber or cylinder of engine 12 means or a circuit 22 for supplying hydraulically-actuating fluid to each injector 20, means or a circuit 24 for supplying fuel to each injector 20, and means or a device 26 for electronically-controlling the fuel system 14. In the embodiment shown, the injectors 20 are preferably unit injectors. Alternatively, the injectors 20 may not be unitized. As shown in FIG. 1, HEUI fuel system 14 further includes means 28 for detecting engine speed, means 30 for detecting actuating fluid temperature, and means 32 for detecting starter voltage. Preferably, the means 28 for detecting engine speed directly detects the angular speed of the engine crankshaft. Alternatively, the means 28 may detect engine speed by detecting the speed of another engine component, such as a crankshaft whose motion is synchronized with the motion of the engine crankshaft.

As shown in FIG. 1, means 15 for providing starter voltage may preferably take the form of a lead acid battery 34. The means 17 for selectively applying starter voltage may include starter switch 36.

Figure 3:
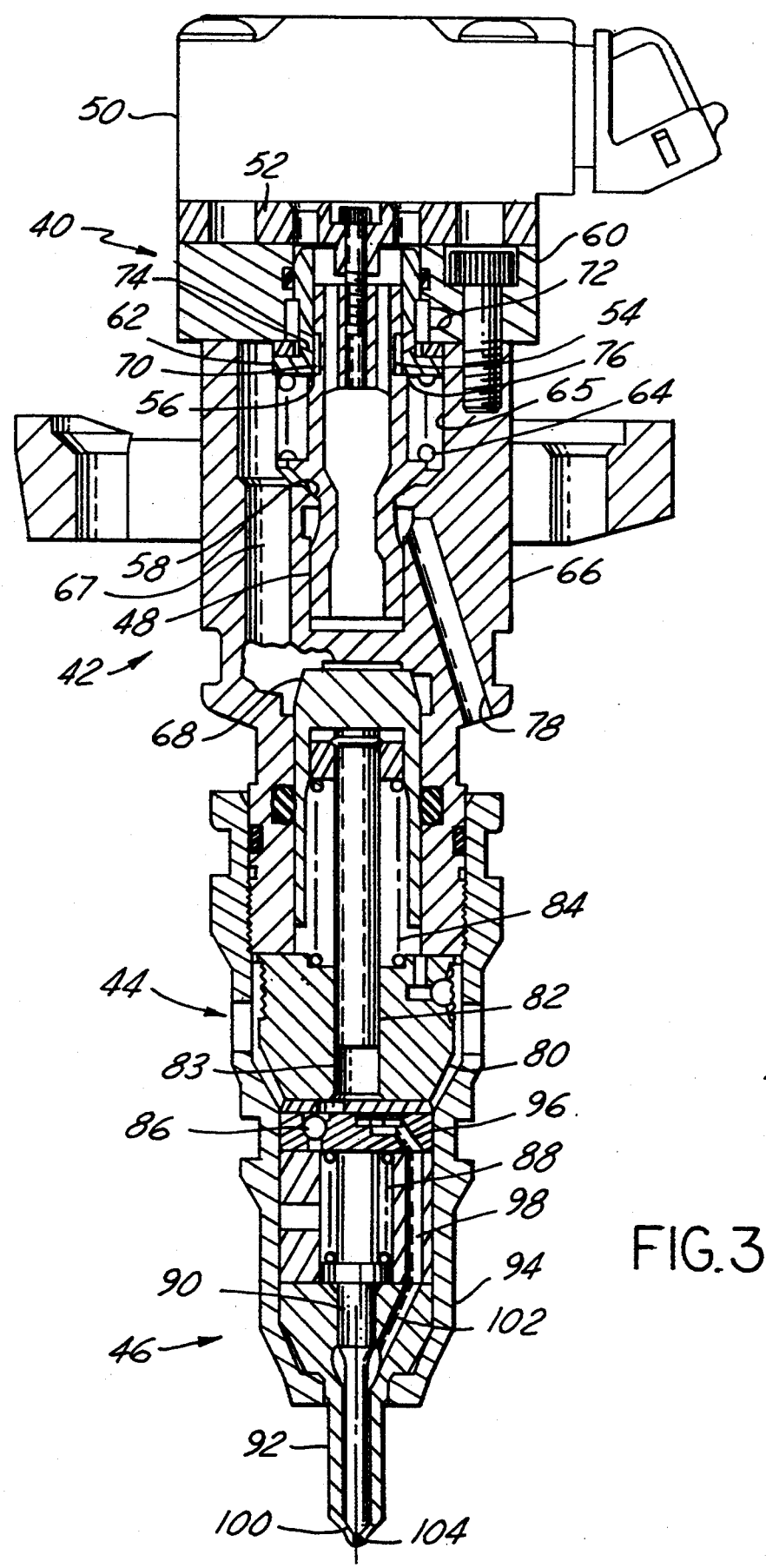
FIG. 3 is an enlarged longitudinal sectional view of one of the injectors shown in FIGS. 1-2.

As shown in FIG. 3, each HEUI injector 20 has a longitudinal axis 38 and includes an actuator and valve assembly 40, a body assembly 42, a barrel assembly 44, and a nozzle and tip assembly 46.

The actuator and valve assembly 40 is provided for selectively communicating relatively-high-pressure actuating fluid to each injector 20 in response to receiving signal $S_{10}$ shown in FIG. 2. The actuator and valve assembly 40 preferably includes popper valve 48, fixed stator 50, and movable armature 52 connected to the popper valve 48. Popper valve 48 includes an upper annular peripheral groove 54, an annular upper seat 56, and an annular lower seat 58.

As shown in FIG. 3, the body assembly 42 includes a popper adapter 60, a popper sleeve 62, a popper spring 64, a popper spring cavity 65, a piston and valve body 66, an actuating fluid intermediate passage 67, and an intensifier piston 68. The popper adapter 60 has a main bore formed therethrough, and a counterbore formed on the lower end portion of the main bore. An annular drain passage 70 is defined between popper sleeve 62 and the counterbore of popper adapter 60. The popper adapter 60 also has a drain passage 72 defined therein. Preferably, the actuating fluid is chosen to be engine lubricating oil wherein drain passage 72 is adapted to communicate with an engine lubricating oil sump. Alternatively, the actuating fluid may be fuel wherein drain passage 72 is adapted to communicate with the fuel supply circuit 24.

As shown in FIG. 3, popper sleeve 62 has at least one, and preferably two, laterally extending passages 74 formed therein. The popper sleeve 62 has an annular shoulder formed on a lower end wherein an annular seat 76 is formed. The piston and valve body 66 has formed therein an actuating fluid inlet passage 78.

As shown in FIG. 3, the barrel assembly 44 includes barrel 80, plunger 82, plunger chamber 83, and plunger spring 84. The nozzle and tip assembly 46 includes an inlet flow check valve 86, a needle check spring 88, an axially movable needle check or valve 90, a needle check tip 92, a case 94, a first discharge passage 96, and a second discharge passage 98.

The needle check tip 92 includes an annular seat 100, a discharge passage 102, and at least one, but preferably a plurality of, fuel injection spray orifices 104. In the embodiment of FIG. 2, the means or device 22 for supplying hydraulic actuating fluid comprises an actuating fluid sump 106 such as an engine oil pan, an actuating fluid transfer pump 108, an actuating fluid cooler 110, an actuating fluid filter 111, a relatively-high-pressure actuating fluid pump 112, a pressure regulator 113, a high-pressure actuating fluid manifold 114 for each bank of injectors 20, a manifold supply passage 116, and a return line 118.

As shown in FIG. 2, means or device 24 for supplying fuel to injector 20 comprises a fuel tank 120, a fuel transfer and priming pump 122, a fuel manifold 124 for each bank of injectors 20, and a return line 126.

The means or device 26 for electronically controlling the HEUI fuel system 14 includes a programable electronic control module 128 and a means or device for detecting various operating parameters and generating a respective parameter indicative signal $S_{1-8,11}$, hereinafter referred to as an input data signal, the data signal being indicative of the parameter detected. The detecting and generating means preferably includes one or more conventional sensors or transducers which periodically detect one or more parameters and generate corresponding data signals that are provided as inputs to electronic control module 128. Preferably, the input data signals include engine speed $S_1$, engine crankshaft position $S_2$, engine coolant temperature $S_3$, engine exhaust back pressure $S_4$, air intake manifold pressure $S_5$, actuating fluid pressure $S_6$, throttle position setting $S_7$, and battery voltage $S_{11}$. If engine 12 is coupled to an automatic transmission, $S_8$ may be defined, for example, as a gear setting of the transmission. Control module 128 is provided with a memory means for storing a variety of predetermined operating data and preferably takes the form of Read-Only Memory (ROM) 129.

Control module 128 generates two output command signals. 0no output control signal, $S_9$, is the actuating fluid manifold pressure command signal. The pressure command signal $S_9$ is provided as an input to pressure regulator 113 to adjust the output pressure of high-pressure pump 112. In order to accurately control the actuating fluid pressure, a sensor is provided for detecting the pressure of the hydraulically actuating fluid supplied to injectors 20 to generate the pressure indicative signal $S_6$. Preferably, the sensor detects the pressure of the actuating fluid in the manifold 114. The control module 128 compares the actual actuating fluid pressure with the desired pressure and makes any necessary correction to control signal $S_9$. The control signal $S_9$ determines the pressure of the actuating fluid in manifold 114 and consequently determines the pressure of the fuel injected during each injection phase or cycle independent of engine speed and load.

The other output control signal, $S_{10}$, is the fuel delivery command signal which is supplied to each injector 20. The fuel delivery command signal $S_{10}$ determines the time for starting fuel injection and quantity of such fuel injection during each injection phase or cycle independent of engine speed and load.

As shown in FIG. 1, the means 28 for detecting crankshaft speed preferably includes a crankshaft position sensor 130, the means 30 for detecting actuating fluid temperature preferably includes an engine coolant temperature sensor 132, and the means 32 for detecting starter voltage preferably includes voltage sensor 134.

The operation of injector 20 will now be described. High-pressure actuating fluid is supplied by high-pressure pump 112 to inlet passage 78 of body 66. When the actuator and valve assembly 40 of the injector 20 is in a de-energized state, popper valve 48 is in a first position wherein lower seat 58 abuts body 66, thus blocking the communication of the high-pressure actuating fluid to the popper spring cavity 65 and intensifier piston 68. In the first position, since the fluid near the top of intensifier piston 68 is in communication with an actuating fluid sump by way of annular drain passage 70, laterally extending passages 74, and drain passage 72, the force exerted by plunger spring 84 displaces intensifier piston 68 to a first or upper position abutting body 66.

To begin injection, control module 128 applies a fuel delivery command signal $S_{10}$ which places a selected injector 20 in an energized state wherein armature 52 is magnetically drawn towards stator 50. Popper valve 48 moves with armature 52, and is thus also drawn towards stator 50. The popper valve 48 moves upwardly along longitudinal axis 38 until annular upper seat 56 abuts annular seat 76 of popper sleeve 62 to define a second position. In the second position, annular lower seat 58 no longer abuts body 66, and high-pressure actuating fluid is admitted to the poppet spring cavity 65 and the passage 67 communicating with the intensifier piston 68. The passage 67 to intensifier piston 68 no longer communicates with actuating fluid sump 106 since annular upper seat 56 blocks communication with drain passage 70, and therefore the high-pressure actuating fluid supplied by the manifold 114 hydraulically exerts a downward driving force on the top of intensifier piston 68. As piston 68 and plunger 82 move downward in response to the above-mentioned force, the pressure of the fuel in plunger chamber 83 below plunger 82 increases. The intensification of the fuel pressure to a desired level is achieved through the selected ratio of effective working areas between the intensifier piston 68 and plunger 82. This pressurized fuel flows through discharge passages 96, 98 and 102, wherein the pressurized fuel acts on needle check 90 to lift needle check 90 from annular seat 100 once a selected valve opening pressure is reached. The pressurized fuel is then discharged through fuel injection spray orifices 104.

To end injection, signal $S_{10}$ is discontinued by control module 128 to de-energize injector 20. The absence of a magnetic force acting on armature 52 is effective to allow compressed popper spring 64 to expand causing armature 52 and popper valve 48 to move back to the first position. At the first position, high-pressure actuating fluid is blocked from entering popper spring cavity 65 and passage 67 to intensifier piston 68. Since the passage 67 to the intensifier piston 68 again communicates with actuating fluid sump 106, the fluid pressure therein decreases such that the force of the compressed plunger spring 84 overcomes the relatively smaller force applied by the actuating fluid to the top of intensifier piston 68, wherein compressed plunger spring 84 expands to return plunger 82 and intensifier piston 58 to the upper position against body 66. The pressure of the fuel in plunger chamber 83 below plunger 82 also decreases such that compressed needle check spring 88 moves needle check 90 downwardly against annular seat 100 of needle check tip 92 once a selected valve closing pressure is reached. The upwardly traveling plunger 82 allows inlet fuel to unseat flow check valve 86 to refill the plunger chamber 83.

Industrial Applicability

The viscosity of the actuating fluid used to actuate a hydraulically-actuated fuel injector varies inversely with the actuating fluid temperature. Under cold engine starting conditions, this increase in viscosity due to relatively lower temperatures affects the timing, quantity and pressure of fuel delivered to an engine combustion chamber during an injection phase or cycle. One approach for compensating for this increased viscosity by inferring a typical viscosity through measuring the ambient temperature. If the type of actuating fluid is known, the system works satisfactorily. With the advent of hydraulically-actuated injectors that use engine lubricating oil as the actuating fluid, however, the above approach has proven inadequate. Since the choice of engine lubricating oil remains with the user, the viscosity variability introduced by the use of varying grades of oil makes use of a fuel injection control system with viscosity variation compensation based only on temperature unsatisfactory.

Before proceeding to a description of the method of detecting actuating fluid viscosity, several pertinent features of internal combustion engine system 10 will be discussed. It may be appreciated that there exists a time interval between the initial application of fuel delivery command signal $S_{10}$ and the time when pressurized fuel begins to flow through fuel injection spray orifices 104. An increase in the viscosity of the actuating fluid results in greater pressure drops of the actuating fluid throughout the actuating fluid circuit 22. As shown in FIG. 3, the circuit includes the several passages through which actuating fluid must flow to reach intensifier piston 68 of the injector 20. Since the pressure of the fluid supplied to the top of intensifier piston 68 is lower than would nominally be expected, the fuel pressurization phase takes a greater period of time to complete, and thus the fuel injection occurs later than expected relative to a predetermined crankshaft angle. Therefore, to compensate for the retarded fuel injection event, fuel delivery command signal $S_{10}$ must be advanced relative to a nominal time.

The quantity and pressure of fuel delivered is also affected by changes in the viscosity of the actuating fluid. As was discussed above, because of pressure drops due to the increased viscosity of the actuating fluid, intensifier piston 68 moves downwardly along axis 38 more slowly than would nominally be expected. Since a predetermined pulsewidth or duration of fuel delivery command signal $S_{10}$ would be expected to result in a predetermined downward travel of plunger 82, corresponding to a predetermined quantity of fuel being injected, the slower downward movement of plunger 82 results in less downward travel before the predetermined pulsewidth is discontinued. Since the quantity of fuel displaced is smaller, less fuel is injected. The pulsewidth of fuel delivery command signal $S_{10}$ can be increased by control module 128 to compensate for this abbreviated downward travel of plunger 82.

For a typical engine oil grade, control module 128 uses programmed data stored in memory means 129 to apply fuel delivery command signal $S_{10}$ to a selected injector 20 at a predetermined time with respect to an angular position of crankshaft 18 and for a predetermined duration or pulsewidth. This predetermined timing and pulsewidth have values which are a function of the actuating fluid temperature.

In the foregoing description, exemplary methods of compensating for a known viscosity increase were explained. In the alternative, the pressure of the actuating fluid may be relatively increased to compensate for the anticipated incremental pressure drops associated with the incremental increase in actuating fluid viscosity. For a typical engine oil grade, control module 128 uses programmed data stored in memory means 129 to regulate the output pressure of high-pressure pump 112 to a predetermined value, this value being a function of the actuating fluid temperature. This solution results in supplying actuating fluid to the top of intensifier piston 68 of a pressure such that timing, delivery and pressure parameters of injector 20 are not affected by viscosity variations.

Although prior art systems have detected the viscosity of various fluids, the output of many of such systems is not in a form easily useable by conventional microcontrollers or microcomputers that, increasingly, control state-of-the-art fuel injection systems (e.g., the output may be a force that controls a valve). Accordingly, this invention preferably measures various physical parameters of engine system 10 and uses that information to generate a signal or parameter easily useable by control module 128. To this end, it should be noted that the primary loads on an engine starter motor, at relatively low temperatures, are viscose loads (e.g., the shearing of oil as engine parts move through and against the oil). Assuming that most of the observed variation in crankshaft angular speed of rotation, as measured in revolutions per minute (R.P.M.), when starting an engine is caused by lubricating oil viscosity changes, then the observed engine crankshaft angular speed will be proportional to engine lubricating oil viscosity, and thus, also, to the actuating fluid viscosity since the fluids are preferably the same. For example, assume that at +20° C. (68° F.), a typical angular speed of the engine crankshaft might be 250 R.P.M. for a fluid with a known viscosity. If, when the temperature is −20° C. (−4° F.), the crankshaft speed is 100 R.P.M., then the viscosity of that fluid can be approximated by normalizing the cold crankshaft speed to the warm crankshaft speed and scaling the known viscosity accordingly.

Referring to FIG. 1, engine crankshaft angular speed is determined by control module 128 in accordance with input data signal $S_2$ from crankshaft position sensor 130. Preferably, crankshaft position sensor 130 takes the form of unique milling or slots formed on the end of a conventional camshaft of engine 12, and a conventional transducer responsive to the angular rotation of the slots to generate camshaft position information. Since the camshaft and crankshaft 18 rotate together, in fixed angular relation, the angular position of crankshaft 18 can be determined. As may be readily appreciated by those of ordinary skill in the art, crankshaft angular speed can be determined from crankshaft angular position in conjunction with clock data from a conventional clock or timing means (not shown).

Since actuating fluid viscosity varies with temperature, the actuating fluid viscosity may be used to update viscosity with temperature changes. Although it should be understood that the actuating fluid temperature can be measured directly by conventional sensors, preferably the actuating fluid temperature is determined by detecting the temperature of the engine coolant fluid. The engine coolant temperature sensor 132 provides data signal $S_3$ as an input to control module 128. Actuating fluid temperature is either assumed to be the same or is more precisely determined by adjusting the engine coolant temperature by a predetermined scaling factor stored in memory means 129.

Typical lead acid batteries, such as battery 34 shown in FIG. 1, are also affected by relatively low temperatures, the effects taking the form of reduced output voltage and current sourcing capacity. Failure to consider this decrease in battery voltage would lead to skewed results because the observed decrease in engine crankshaft angular speed is due not only to increased actuating fluid viscosity, but is also due to the decrease in the battery voltage to engine starter motor 16. Therefore, the voltage applied to starter motor 16 must also be determined and considered to calculate actuating fluid viscosity.

Preferably, as shown in FIG. 1, means 32 for detecting starter voltage includes voltage sensor 34, which detects the voltage applied to engine starter motor 16 when starter switch 36 is closed to generate an input data signal $S_{11}$ indicative of the voltage detected.

The inventive method of determining viscosity in an internal combustion engine system 10 will now be described. As shown in FIG. 1, electronic control module 128 is responsive to input data signals $S_2$, $S_3$ and $S_{11}$ and memory means 129. When switch 36 is closed, voltage provided by battery 34 is supplied to engine starter motor 16, which causes motor 16 to rotate crankshaft 18 through coupling means 19. Once crankshaft 18 begins to rotate, crankshaft position sensor 130 provides crankshaft position indicative signal $S_2$ as an input to control module 128. Preferably, a predetermined number of rotations occur before control module 128 calculates the speed of crankshaft 18 since it is desirable for crankshaft 18 to have reached a steady state speed during cranking. Control module 128 then calculates the angular speed of rotation of crankshaft 18 using signal $S_2$. The control module 128 then measures the voltage applied to starter motor 16 using voltage indicative signal $S_{11}$ generated by voltage sensor 134. Control module 128 uses the measured applied voltage, and the crankshaft angular speed, along with several constants, to determine actuating fluid viscosity as follows:

$$VIS_1 = \frac{\left( \frac{V^2_{starter}}{R_{starter}} - P \text{ parasitics} \right)}{\rho \frac{(R_c \cdot w)^2}{h} A}$$

WHERE:

$VIS_1$ = the value of the actuating fluid viscosity;

$V_{starter}$ = the measured applied voltage to the engine starter motor 16;

$R_{starter}$ = a resistance value of the starter motor 16;

$P_{parasitics}$ = the total sum of parasitic losses in engine 12 other than viscous losses (e.g., alternator load, transmission drag);

$\rho$ = a predetermined typical density of engine lubricating oil;

$R_c$ = a predetermined crankshaft throw distance (i.e., ½ the stroke of the piston, or the distance from the centerline of crankshaft 18 to the centerline of the crankshaft bearing);

w = the determined crankshaft 18 angular speed;

h = a predetermined radial distance (i.e., the distance between the piston and cylinder wall); and A = a predetermined area of the piston (i.e., the surface area of the piston that is in contact with the cylinder wall, or piston circumference x piston height).

The formula and accompanying constants are stored in memory means 129 accessible by control module 128.

It should be appreciated that each type and grade of engine lubricating oil has its own viscosity characteristics, which vary as function of temperature. Thus, even though the above-determined viscosity value is sufficient to effect the above-mentioned compensations, it may nonetheless be desirable to determine the actual type and grade of lubricating oil being used so that an accurate determination of viscosity can more easily be made with subsequent temperature variations (e.g., engine warm-up). For example, a determined viscosity value may be equivalent to two or more grade and types of engine lubricating oil at two or more respective temperatures. If the temperature at which the viscosity value was determined is known, then the particular grade and type of oil may be identified and also be associated with a known viscosity-temperature curve. As the temperature of the oil changes, the corresponding viscosity value may be found, for example, by merely following the curve to the new temperature, and determining the new viscosity. Thus, preferably, control module 128, then calculates the actuating fluid temperature using engine coolant temperature indicative signal $S_3$ generated by coolant temperature sensor 132, and uses this temperature, in conjunction with the calculated viscosity $VIS_1$, to ascertain the grade and type of engine lubricating oil.

This inventive method of determining viscosity is performed for every start cycle of engine 12. Further, control module 128 is of the type including an internally used viscosity indicative signal or parameter having an initial predetermined value. Therefore, the viscosity parameter will be set to either the predetermined value or the value as determined during prior operation of engine 12. Since the customer may have changed the engine lubricating oil since the conclusion of the prior operating cycle, the type and grade of the engine lubricating oil may have also changed, and the pre-existing viscosity parameter value may not be indicative of the actuating fluid viscosity. Therefore, for every start cycle, the viscosity parameter of control module 128 is preferably adjusted to the most recently determined viscosity value to reset the old viscosity parameter value.

Once the actuating fluid viscosity parameter has been adjusted or updated, control module 128 employs a plurality of processes and control strategies that use the viscosity parameter to optimally control the operation of engine system 10. For example, the pulsewidth of electrical fuel delivery command signal $S_{10}$, the timing of fuel delivery command signal $S_{10}$ relative to a predetermined angular position of crankshaft 18, and the regulated output pressure of high-pressure pump 112 which is proportional to the pressure of fuel injected by the injector 20 all may be selectively varied independent of engine speed and load, as explained earlier, in response to the viscosity indicative signal or parameter. Moreover, while the determined actuating fluid signal may be used throughout the operation of engine system 10, preferably the determined value of the actuating fluid viscosity is utilized only during the start-up of engine 12. Thereafter or once the engine reaches its normal operating temperature range, typical default values are used with the above-described temperature compensation scheme.

A method wherein the pulsewidth of fuel delivery command signal $S_{10}$ is varied to efficiently effect start-up of engine 12 will now be described. After the actuating fluid viscosity, $VIS_1$, has been determined, electronic control module 128, in conjunction with memory means 129, determines an updated pulsewidth value, $T_1$, as a function of $VIS_1$. Control module 128, then adjusts the predetermined pulsewidth to the updated pulsewidth value $T_1$. The electronic control module 128, with predetermined timing relative to an angular position of crankshaft 18, then applies a fuel delivery command signal $S_{10}$ for the updated pulsewidth $T_1$. The high pressure pump 112 then supplies actuating fluid to injector 20 regulated to a predetermined pressure as controlled by actuating fluid manifold pressure command signal $S_9$ to effect delivery of fuel to engine 12, as described above in the paragraphs relating to the operation of injector 20. Upon completion of the updated pulsewidth $T_1$, the electronic control module 128 discontinues the fuel delivery command signal $S_{10}$ to thereby stop delivery of fuel to engine 12.

An alternative method of operating an internal combustion engine system wherein a predetermined timing value is varied will now be described. The electronic control module 128 determines an updated timing value, $TM_1$, as a function of $VIS_1$, and adjusts the predetermined timing to the updated timing value $TM_1$. The control module 128 applies a fuel delivery command signal $S_{10}$ with the updated timing value $TM_1$ for the predetermined pulsewidth and high-pressure pump 112 supplies actuating fluid of the predetermined regulated pressure to the injector 20 to effect delivery of fuel to engine 12. Upon completion of the predetermined pulsewidth, control module 128 discontinues the fuel delivery command signal $S_{10}$ effective to stop delivery of fuel to engine 12.

Still another method of operating internal combustion engine system 10 wherein actuating fluid pressure, and hence fuel injection pressure, is varied will now be described. The electronic control module 128 determines an updated pressure value, $P_1$ as a function of $VIS_1$, and adjusts the predetermined regulated pressure, to the updated pressure value $P_1$. The electronic control module 128, with predetermined timing, then applies a fuel delivery command signal $S_{10}$ for the above-described predetermined pulsewidth. The high pressure pump 112 then supplies actuating fluid of pressure $P_1$ to the injector 20 to effect delivery of fuel to engine 12. Upon completion of the predetermined pulsewidth, electronic control module 128 discontinues the fuel delivery command signal $S_{10}$, which is effective to stop delivery of fuel to engine 12.

Another aspect of the present invention relates to a method of updating the actuating fluid viscosity $VIS_1$, after engine 12 has been started and is running. An advantage of the present invention is that a user's choice of engine lubricating oil grade does not affect the performance of engine system 10. Once $VIS_1$ has been determined and the temperature at which this determination is made is measured, the type and grade of the lubricating oil can be ascertained, as described above. With this information, future values of the actuating fluid viscosity depend primarily only on temperature changes as the engine lubricating oil warms. In this aspect of the present invention, a second actuating fluid viscosity value, $VIS_2$, is determined. The method includes the steps of detecting a change in the actuating fluid temperature and measuring the updated actuating fluid temperature to generate a second viscosity value, $VIS_2$, as a function of $VIS_1$, the initially detected temperature, and the updated actuating fluid temperature, and adjusting the actuating fluid viscosity parameter of control module 128 to the value of $VIS_2$.

Once this new, second viscosity value, $VIS_2$, has been determined, pulsewidth, timing, and pressure can be updated in substantial accordance with the previously described methods, except that another updated pulsewidth value $T_2$, another updated pressure value $P_2$, and another updated timing value $TM_2$, are calculated as a function of $VIS_2$.

It should be understood that although control module 128 determines the value $VIS_1$ for internal use to define the magnitude of the above-mentioned viscosity indicative signal or parameter, alternate uses, for example, generating a viscosity indicative signal external to control module 128 for direct use by various components of engine system 10, are within the spirit and scope of this invention.

One of the main advantages of the present invention is the ability to eliminate the effects of the variability of the viscosity of the actuating fluid used to actuate a hydraulically-actuated electronically controlled injector, such as injector 20. Since this variability can be eliminated, internal combustion engine systems, such as internal combustion engine system 10 are able to operate optimally even though customers periodically change the type and grade of engine lubricating oil. This solution to the problem of customer selected engine lubricating oil allows implementation of control strategies utilizing such fuel injection operating parameters such as injection pulsewidth, actuating fluid pressure and fuel injection pressure, and injection timing, to optimally define a system that can meet modern day emissions and performance goals.

Other aspects, objects, and advantages of this invention can be obtained from a study of the drawings, the disclosure, and the appended claims.

What is claimed:

1. A method of operating an internal combustion engine system, the system comprising a crankshaft and an engine starter motor adapted to rotate the crankshaft, comprising the steps of:
   rotating the crankshaft by applying a voltage to the engine starter motor;
   detecting the angular speed of rotation of the crankshaft to generate an angular speed indicative signal;
   detecting the voltage applied to the engine starter motor to generate a voltage indicative signal;
   determining the value of the viscosity of the actuating fluid using the angular speed indicative signal and the voltage indicative signal, and generating a first viscosity indicative signal; and
   varying at least one of a plurality of fuel injection parameters as a function of the first viscosity indicative signal.

2. The method of claim 1, wherein said plurality of fuel injection parameters comprises a regulated pressure of the actuating fluid, a first selected pulsewidth, and selected timing.

3. The method of claim 2, wherein the system includes an engine, a means for supplying actuating fluid at the predetermined regulated pressure to a hydraulically-actuated injector, means for supplying fuel to the injector, and a controlling means for initiating fuel injection with selected timing with respect to an angular position of the crankshaft for the first selected pulsewidth, and wherein the step of varying at least one of a plurality of fuel injection parameters is performed by the substeps of:
   determining a first updated pressure value selected as a function of the first viscosity indicative signal;
   adjusting the selected regulated pressure to said first updated pressure value;
   applying a first fuel delivery command signal of the first selected pulsewidth to the injector to open a valve for admitting actuating fluid;
   supplying actuating fluid of the first updated pressure to the injector in response to the valve being opened during the first predetermined pulsewidth to effect delivery of fuel to the engine; and
   discontinuing the first fuel delivery command signal upon completion of the first selected pulsewidth to close the valve, the closure of the valve being effective to stop delivery of fuel to the engine.

4. The method of claim 3, wherein the step of varying at least one of a plurality of fuel injection parameters is performed by the further steps of:
   detecting the temperature of the actuating fluid when the first viscosity indicative signal is determined in said viscosity determining step and generating a first temperature indicative signal;
   determining when the first temperature of the actuating fluid has changed to a second temperature;
   generating a second signal indicative of the viscosity of the actuating fluid at the second temperature, the second viscosity indicative signal having a value selected as a function of the first viscosity indicative signal, the first temperature indicative signal and the second temperature;
   determining a second updated pressure value selected as a function of the second viscosity indicative signal;
   adjusting the first updated pressure to the second updated pressure value;
   applying a second fuel delivery command signal of a second selected pulsewidth to the injector to open the valve for admitting actuating fluid;
   supplying actuating fluid of the second updated pressure to the injector in response to the valve being opened during said second selected pulsewidth to effect delivery of fuel to the engine; and
   discontinuing the second fuel delivery command signal upon completion of said second selected pulsewidth to close the valve, the closure of the valve being effective to stop delivery of fuel to the engine.

5. The method of claim 2, wherein the system includes an engine, a means for supplying actuating fluid at the variably selected regulated pressure to an injector, means for supplying fuel to the injector, and a controlling means for initiating fuel injection with variably selected timing with respect to an angular position of the crankshaft for the first predetermined pulsewidth, and wherein the step of varying, at least one of a plurality of fuel injection parameters is performed by the substeps of:
   determining a first updated pulsewidth value selected as a function of the first viscosity indicative signal;
   adjusting the first selected pulsewidth to the first updated pulsewidth value;
   applying a first fuel delivery command signal of the first updated pulsewidth to the injector to open a valve for admitting actuating fluid;
   supplying actuating fluid of the selected regulated pressure to the injector in response to the valve being opened during said first updated pulsewidth to effect delivery of fuel to the engine; and
   discontinuing the first fuel delivery command signal upon completion of the first updated pulsewidth to close the valve, the closure of the valve being effective to stop delivery of fuel to the engine.

6. The method of claim 5, wherein the step of varying at least one of a plurality of fuel injection parameters is performed by the further substeps of:
   detecting the temperature of the actuating fluid when the first viscosity indicative signal is determined in said viscosity determining step and generating a first temperature indicative signal;
   determining when the first temperature of the actuating fluid has changed to a second temperature;
   generating a second signal indicative of the viscosity of the actuating fluid at the second temperature, the second viscosity indicative signal having a value selected as a function of the first viscosity indicative signal, the first temperature indicative signal, and the second temperature;

determining a second updated pulsewidth value selected as a function of the second viscosity indicative signal;

adjusting the first updated pulsewidth to the second updated pulsewidth value;

applying a second fuel delivery command signal of the second updated pulsewidth to the injector to open the valve for admitting actuating fluid;

supplying actuating fluid of the selected regulated pressure to the injector in response to the valve being opened during said second updated pulsewidth to effect delivery of fuel to the engine; and discontinuing the second fuel delivery command signal upon completion of the second updated pulsewidth to close the valve, the closure of the valve being effective to stop delivery of fuel to the engine.

7. The method of claim 2, wherein the system includes an engine, a means for supplying actuating fluid at the predetermined regulated pressure to an injector, means for supplying fuel to the injector, and a controlling means for initiating fuel injection with variably selected timing with respect to an angular position of the crankshaft for the first selected pulsewidth, and wherein the step of varying at least one of a plurality of fuel injection parameters is performed by the substeps of:

determining a first updated timing value selected as a function of the first viscosity indicative signal;

adjusting the selected timing to the first updated timing value;

applying a first fuel delivery command signal with the first updated timing of the first selected pulsewidth to the injector to open a valve for admitting actuating fluid;

supplying actuating fluid of the selected regulated pressure to the injector in response to the valve being opened during the first selected pulsewidth to effect delivery of fuel to the engine; and discontinuing the first fuel delivery command signal upon completion of the first selected pulsewidth to close the valve, the closure of valve being effective to stop delivery of fuel to the engine.

8. The method of claim 7, wherein the step of varying at least one of a plurality of fuel injection parameters is performed by the further substeps of:

detecting the temperature of the actuating fluid when the first viscosity indicative signal is determined in said viscosity determining step and generating a first temperature indicative signal;

determining when the first temperature of the actuating fluid has changed to a second temperature;

generating a second signal indicative of the viscosity of the actuating fluid at the second temperature, the second viscosity indicative signal having a value selected as a function of the first viscosity indicative signal, the first temperature indicative signal, and the second temperature;

determining a second updated timing value selected as a function of the second viscosity indicative signal;

adjusting the first updated timing to the second updated timing value;

applying a second fuel delivery command signal with the second updated timing of a second predetermined pulsewidth to the injector to open the valve for admitting actuating fluid;

supplying actuating fluid of the predetermined regulated pressure to the injector in response to the valve being opened during the second predetermined pulsewidth to effect delivery of fuel to the engine; and discontinuing the second fuel delivery command signal upon completion of the second predetermined pulsewidth to close the valve, the closure of valve effective to stop delivery of fuel to the engine.

9. A method of detecting viscosity of actuating fluid in a engine system having a crankshaft and an engine starter motor adapted to rotate the crankshaft, comprising the steps of:

rotating the crankshaft by applying a voltage to the engine starter motor;

generating an angular speed indicative signal, including detecting an angular speed of rotation of the crankshaft rotated by the engine starter motor;

generating a voltage indicative signal by detecting said voltage applied to the engine starter motor; and generating a viscosity indicative signal indicating the viscosity of the actuating fluid, using the voltage indicative signal and the angular speed indicative signal.

10. The method of claim 9 including the steps of:

detecting a first temperature of the actuating fluid to generate a first temperature indicative signal;

determining the type and grade of the actuating fluid using the viscosity indicative signal and the first temperature signal;

determining when the first temperature of the actuating fluid has changed to a second temperature;

generating an updated viscosity indicative signal indicative of the viscosity of the actuating fluid at the second temperature, the updated viscosity indicative signal having a value selected as a function of the determined type and grade of the actuating fluid and the second temperature.

11. The method of claim 9 wherein said actuating fluid is engine lubricating oil.

12. An apparatus for detecting the viscosity of actuating fluid in an engine system, said engine system having a crankshaft and an engine starter motor adapted to rotate the crankshaft, comprising:

means for rotating said crankshaft when a voltage is applied to said engine starter motor;

means responsive to rotation of said crankshaft for detecting an angular speed of rotation of said crankshaft and for generating an angular speed indicative signal related to said angular speed of rotation of said crankshaft;

means responsive to said applied voltage for detecting said voltage applied to said engine starter motor and for generating a voltage indicative signal; and means responsive to said angular speed indicative signal and said voltage indicative signal for determining the viscosity of said actuating fluid and for generating a viscosity indicative signal.

13. The apparatus of claim 12, further comprising:

means for detecting a first temperature of said actuating fluid and for generating a first temperature indicative signal;

means responsive to said first temperature indicative signal and said viscosity indicative signal for determining type and grade of said actuating fluid;

means for determining when said first temperature of said actuating fluid has changed to a second temperature, and for generating a second temperature indicative signal; and means responsive to said determined type and grade of said actuating fluid and said second temperature indicative signal for generating an updated viscosity indicative signal wherein said updated viscosity indicative signal is determined as a function of said determined type and grade of actuating fluid and said second temperature indicative signal.

14. A method of operating a hydraulically-actuated electronically-controlled fuel system adapted for an engine having a moveable component whose motion is indicative of engine speed and which moves through actuating fluid, comprising the steps of:

moving the component through the actuating fluid by applying a voltage to an engine starter motor;

detecting the angular speed of movement of the component to generate an angular speed indicative signal;

detecting the voltage applied to the engine starter motor to generate a voltage indicative signal;

determining the value of the viscosity of the actuating fluid using the angular speed indicative signal and the voltage indicative signal, and generating a first viscosity indicative signal; and varying at least one of a plurality of fuel injection parameters as a function of the first viscosity indicative signal.

15. A hydraulically-actuated electronically controlled fuel injection system adapted for an engine having a moveable component whose motion is indicative of engine speed and which moves through actuating fluid, said component being rotatable by an engine starter motor comprising:

means for moving said moveable component through said actuating fluid when a voltage is applied to said engine starter motor;

means responsive to the movement of said component for detecting an angular speed of rotation of said component and for generating an angular speed indicative signal;

means responsive to said applied voltage for detecting said voltage applied to said engine starter motor and for generating a voltage indicative signal; and means responsive to said angular speed indicative signal and said voltage indicative signal for determining the viscosity of said actuating fluid and for generating a viscosity indicative signal.

* * * * *